United States Patent
Causey, III

Patent Number: 5,554,174
Date of Patent: Sep. 10, 1996

[54] SYSTEM AND METHOD FOR AUTOMATICALLY ADJUSTING CARDIOVERTER AND DEFIBRILLATOR SHOCK ENERGY AS A FUNCTION OF TIME-TO-THERAPY

[75] Inventor: James D. Causey, III, Simi Valley, Calif.

[73] Assignee: Pacesetter, Inc., Sylmar, Calif.

[21] Appl. No.: 544,524

[22] Filed: Oct. 18, 1995

[51] Int. Cl.$^6$ ........................................... A61N 1/39
[52] U.S. Cl. ............................................ 607/5; 607/7
[58] Field of Search ..................................... 607/5, 7, 8

[56] References Cited

U.S. PATENT DOCUMENTS

| | | | |
|---|---|---|---|
| 5,191,884 | 3/1993 | Gilli et al. ................................. | 607/5 |
| 5,411,537 | 5/1995 | Munshi et al. ............................. | 607/33 |
| 5,488,553 | 1/1996 | Renger ..................................... | 607/7 |

FOREIGN PATENT DOCUMENTS 2265312  9/1993  United Kingdom ....................... 607/5

Primary Examiner—William E. Kamm
Assistant Examiner—Carl H. Layno
Attorney, Agent, or Firm—Lisa P. Weinberg

[57] ABSTRACT

An implantable cardiac device for providing cardioversion and defibrillation therapies is provided, which forecasts time-to-therapy based on battery voltage degradation and provides an enhanced energy shock in the event a predetermined threshold time is reached. The device also monitors elapsed time-to-therapy to determine whether the predetermined threshold time is exceeded and sets the energy content of the therapeutic shock accordingly.

15 Claims, 2 Drawing Sheets

SYSTEM AND METHOD FOR AUTOMATICALLY ADJUSTING CARDIOVERTER AND DEFIBRILLATOR SHOCK ENERGY AS A FUNCTION OF TIME-TO-THERAPY

BACKGROUND OF THE INVENTION

This invention relates to cardiac stimulating devices and particularly to implantable cardiac stimulating devices that deliver therapeutic shocks to cardiac tissue to interrupt pathological cardiac arrhythmias. More particularly, this invention is directed to a system and method for increasing the energy content of a therapeutic cardioversion or defibrillation shock as a function of any time delay from the initial onset of an arrhythmia to the time treatment will be administered.

The typical adult sinus rhythm range is between about 65 and about 85 heartbeats per minute (bpm). Generally, rates between 60 and 100 bpm are not a cause for concern. This range is referred to as the normal sinus rate range. Rates falling outside the sinus rate range are known as arrhythmias. An arrhythmia in which the sinus rate is above 100 bpm is called a tachycardia. An arrhythmia in which the sinus rate is below 60 bpm is called a bradycardia.

Common ventricular arrhythmias include ventricular tachycardia (VT) and ventricular fibrillation (VF). Ventricular arrhythmias are generally considered to be of greater concern than other types of arrhythmias due to the resultant loss of a substantial amount of cardiac output.

VT is a condition where an abnormally high ventricular heart rate severely affects the ability of the heart to pump blood. VT may result in a loss of consciousness due to a decrease in cardiac output. Sustained episodes of VT are particularly dangerous because they may deteriorate into VF.

VF is the most life threatening arrhythmia. VF is the result of rapid and disordered stimulation of the ventricles which prevents them from contracting in a coordinated fashion. This results in a severe drop in cardiac output as the pumping ability of the ventricles is compromised. VF leads to tissue narcosis due to the lack of an oxygenated blood supply and may result in the death of the individual within minutes if left untreated. An effective method of terminating VF is internal or external defibrillation, using a high energy electrical shock provided by an implantable or external defibrillator.

Defibrillators are a species of cardioverters. In contrast to pacemakers, cardioverters deliver a relatively high energy shock to the myocardial tissue. Among cardioverters, defibrillators administer shocks having the greatest energy content. Both cardioverters and defibrillators discharge a relatively large electrical shock across the heart in order to simultaneously depolarize all myocardial tissue. This allows the heart's SA node, which has the fastest spontaneous discharge cells and acts as the heart's natural pacemaker, to regain pacing control and return the heart to within the normal sinus rhythm range. While cardioversion is used for tachycardias of varying rates and severity, defibrillation is only used when the heart is fibrillating.

Generally, during cardioversion, a therapeutic electrical charge is delivered at about the same time a QRS complex occurs—to prevent the possibility of aggravating a tachycardia by either accelerating its frequency or by inducing the heart into ventricular fibrillation. Therapeutic cardioversion energies have a wide range—typically from about 0.05 joules to about 10 joules. During fibrillation the heart quivers instead of beats. Thus, defibrillation shocks, in contrast to cardioversion shocks, cannot be synchronized with a QRS complex because the QRS complexes are not discernable. Typical defibrillation energies range from about 5 joules to about 40 joules. It is desirable to expose the patient to the least amount of energy and the least number of shocks while maintaining a high probability of terminating the arrhythmia.

The lack of a suitable energy source was a major impediment to the development of modern implantable cardiac devices and particularly cardioverter-defibrillators. Initially, mercury zinc and later lithium iodine cells were used, but they were unable to provide the peak current requirements for cardioverter-defibrillators, which typically are in the range from about one to about two amperes for approximately 10 seconds. Lithium vanadium pentoxide batteries were able to meet this requirement, but had a characteristic precipitous voltage decline towards the end of their useable life. These batteries were abandoned because of the difficulty in accurately determining the remaining life of the battery. Currently, lithium silver vanadium pentoxide cells are favored for two reasons: (1) they have greater energy density (i.e., more milliampere-hours stored per unit of battery volume combined with a lower internal resistance); and (2) they have a gradual voltage decline over their usable life. The latter characteristic allows for a more accurate prediction of when the battery's useable life is near its end. However, as will be discussed below, because battery voltage declines with use and time, the time needed to develop high voltage across a capacitor increases as the battery ages. This principle is true for all types of batteries since all batteries suffer from that same limitation—namely, that available energy invariably decreases with time and usage.

Because the cardioversion or defibrillation voltage required is higher than available battery voltages, which are typically on the order of 6.4 volts (two 3.2 volt cells in series), a DC/DC converter is typically used to develop high voltages. The DC/DC oscillator takes the battery voltage and produces a high frequency pulsed voltage substantially equal in magnitude to the battery voltage. This high frequency pulsed voltage is converted by the DC/DC converter to high voltage typically by using a "step-up" transformer. This high frequency, high voltage is then full-wave rectified. The rectified voltage is applied to a pair of high voltage capacitors which charge incrementally with each rectified voltage pulse. Double anode aluminum electrolytic capacitors are typically used in modern cardiac devices.

When an implantable cardiac device senses fibrillation, a finite amount of time is required to charge the capacitors to their target voltage which can be preselected by a physician. The charge time of the capacitors is dependent upon any remaining charge from a previous high voltage therapy event or capacitor reformation, the battery current and voltage, and the combined capacitance of the capacitors. As a consequence, when battery voltage or current output decreases, it takes longer to develop the desired target voltage on the capacitors. This directly translates to a longer time-to-therapy because the cardioverter-defibrillator waits for the capacitor to charge to the target voltage before delivering the shock. Typically, at least two capacitors are used in series to facilitate higher energy storage for monophasic and biphasic pulses of varying waveforms and to allow for administering of sequential pulses, as well as to ensure that sequential pulses are of the same amplitude.

Among the latest improvements in implantable cardiac stimulating devices are tiered therapy systems. These systems typically allow for the administration by a single device of anti-tachycardia pacing therapy in addition to cardioversion and defibrillation therapies. U.S. Pat. No. 4,830,006 issued May 16, 1989 to Haluska et al. describes such a device. These systems can be programmed to administer a number of consecutive cardioversion or defibrillation therapies with each subsequent therapy having an increased level of aggressiveness. When the initial therapy has little or no therapeutic effect, therapy is re-administered. Each time therapy is re-administered, the device may need to cycle through the sensing, charging and delivery cycle. The time delay due to past failed therapy applications can be extensive.

Time-to-therapy can be a determining factor in the efficacy of a therapeutic shock. Echt et al. studied the effects of prolonging time-to-therapy. (D. Echt, J. T. Barbey, J. N. Black, *Influence of Ventricular Fibrillation Duration on Defibrillation Energy in Dogs Using Bidirectional Pulse Discharges,* 11 PACE No. 9, 1315, Sep. 1988.) The results of this study indicate that the energy requirement for an efficacious defibrillation shock at thirty seconds of ventricular fibrillation is significantly greater than at five seconds of fibrillation.

Although previously known devices increase the therapeutic shock energy after failed attempts, they do not adjust the therapeutic shock energy to a greater value after the time-to-therapy has exceeded a predetermined or calculated critical time. Previously known devices also do not compensate for delays in administering therapy caused by inherent device characteristics. In addition, current devices do not provide a way of forecasting the time-to-therapy in order to set an appropriate energy value in advance of a cardiac event.

What is needed, therefore, is an automatic implantable cardiac stimulating device that forecasts the time delay between the onset of a tachyarrhythmia episode and the delivery of therapy. The device should determine the need for an increased energy shock on the basis of a comparison between a forecasted time-to-therapy and a predetermined critical time. In addition, an implantable cardiac stimulating device is needed that determines an actual elapsed time-to-therapy (i.e., from the initial onset of an arrhythmia to the time a therapeutic shock is delivered) and compares that elapsed time-to-therapy with the critical time to determine if an increased energy shock is required.

SUMMARY OF THE INVENTION

The disadvantages and limitations of previously known devices are overcome by the present invention. With this invention, an improved automatic implantable cardiac stimulating device that computes a forecasted time-to-therapy by monitoring certain device operational parameters and that provides an increased energy shock in the event the forecasted time-to-therapy exceeds a predetermined critical time is provided, without the need for additional hardware. In addition, this invention can also determine the need for an increased energy shock by recording the elapsed time between the onset of a tachyarrhythmia episode and the time therapy is administered, and comparing that elapsed time with a predetermined critical time.

It has been realized that in order to achieve a given probability of success, the shock energy must be increased significantly after a certain amount of time has passed after the onset of a tachyarrhythmia. The present invention operates to ensure that only shocks having a high probability of success are delivered. Patients benefit from the present invention, because the first therapeutic shock delivered has a high probability of terminating the arrhythmia. In addition, by delivering only shocks that have a high probability of success, battery energy is conserved, because energy is not needlessly expended on initial failed therapies. By conserving energy in this manner, battery life is prolonged.

The present invention monitors actual battery performance and uses that data to compute a forecasted time-to-therapy based upon, at least in part, the time it will take to charge a pair of capacitors to a target potential. The present invention also determines the total elapsed time from the onset of a tachyarrhythmia to just prior to the delivery of a therapeutic shock. The forecasted time-to-therapy and the elapsed time-to-therapy are compared to a critical time to determine the need for an increased energy therapeutic charge.

The critical time is not a permanently set value. Rather, the physiological differences among individuals and the numerous causes of arrhythmias dictate that the physician, being most knowledgeable about the circumstances, be given deference regarding the selection of the critical time. The physician is also given deference in choosing the energy content of a shock and the way it is increased. For example, the energy content of a shock may be increased by increasing the amplitude of the shock, increasing the pulse width, or decreasing the percent tilt of a waveform.

A preferred embodiment of a device that incorporates the present invention includes two functionally discrete circuits. The first circuit contains low voltage circuitry for delivering pacing therapy to alleviate bradycardia, and low voltage control and logic circuitry to provide overall operational control of the entire device. The other circuit includes low and high voltage circuitry dedicated to the generation and delivery of high energy charges for cardioversion and defibrillation shocks.

The low voltage circuitry of a preferred embodiment include a microprocessor and logic control circuit that communicates with a defibrillation shock delivery control circuit and a DC/DC converter control circuit through a serial interface. The serial interface also allows the two control circuits to communicate with each other. The DC/DC converter control circuit performs the power conversion necessary to create a high voltage charge on a pair of capacitors. The defibrillation shock delivery control circuit performs the logic operations necessary for timing the delivery of a defibrillation or cardioversion shock, and determining the waveform and energy content of that shock. The defibrillation shock delivery control circuit and the DC/DC converter control circuit communicate with a shock delivery circuit on the high voltage side of the device by way of an isolation circuit.

The isolation circuit separates the low voltage circuits of the device (responsible for control and logic operations) from the high voltage circuits of the device (responsible for executing control and logic operations). The isolation circuit prevents low voltage logic circuits from being harmed by the high voltage operations of the device, while allowing for communication between the low voltage circuits and the high voltage circuits. Electrical isolation of the high and low voltage is preferably provided by a transformer interface and resistor/divider networks.

The shock delivery circuit executes instructions transmitted by the two control circuits and creates a high voltage charge. A high voltage charge is created preferably by oscillating a DC voltage supplied by a battery, and passing the oscillated voltage through a DC/DC converter containing a step-up transformer to produce a high frequency, high voltage. The high frequency, high voltage is rectified by a pair of diodes to create a high DC voltage. By exposing two high voltage capacitors in series with each other to the high DC voltage produced by the DC/DC converter and diodes, a high voltage charge is stored and is then ready to be delivered. The shock delivery circuit serves the added function of informing the defibrillation shock delivery control circuit via the isolation circuit that a charge has been generated and is ready to be delivered.

A voltage monitoring circuit is connected across the battery to monitor battery voltage.

The voltage of the high voltage charge is communicated to the microprocessor and logic control circuit through the isolation circuit and the serial interface. The microprocessor and logic control circuit may constantly monitor the actual high DC voltage or preferably may periodically interrogate the voltage monitoring circuit at predetermined intervals.

In accordance with the present invention, the energy level of the therapeutic shock is selected by the microprocessor and logic control so that the first delivered shock has a high probability of terminating the arrhythmia. If the microprocessor and logic control circuit determines that due to battery depletion, the forecasted time-to-therapy equals or exceeds the predetermined critical time, it automatically sets the shock energy to an increased level. That level is communicated to the defibrillation shock delivery control circuit through the serial interface. The defibrillation shock delivery control circuit instructs the shock delivery circuit, through the isolation circuit, as to what the energy level of the shock should be. Delivering a shock of a lower energy value having a lower probability of success is thereby avoided, and battery energy may be conserved.

The implantable cardiac stimulating device of the present invention preferably incorporates a timer (time-to-therapy timer) that accumulates time from the point of detection of the ventricular tachyarrhythmia until the time-to-therapy timer reaches a preprogrammed maximum count or the tachyarrhythmia is terminated by therapy or spontaneously terminates.

When the tachyarrhythmia is detected, software operating within the microprocessor, RAM and ROM, selects the first stage of the first tier of therapy. The first tier of therapy may be typically programmed to be antitachycardia pacing (ATP). The time-to-therapy timer continues to accumulate time while ATP therapy is delivered. If the tachyarrhythmia is sustained following the ATP attempt, the software may be programmed to select the first shock therapy in a sequence of shock therapies. The sequence of shock therapies is typically ordered with regard to increasing stored energy. Shock 1 may be 10 joules, shock 2 may be 20 joules, and shocks 3 and 4 may be 40 joules. If the time-to-therapy timer has reached a programmed maximum when the software selects shock 1, the software shall bypass the lower energy shocks (shock 1 and shock 2) and select shock 3. By substituting shock 3 for shock 1 as the first shock, the first shock is more likely to be efficacious than the programmed lower energy shock 1 due to the delay during the ineffective ATP attempt.

When the ventricular tachyarrhythmia is terminated, the time-to-therapy timer is reset to zero and the shock 1, 2, 3, 4 sequence of shock therapies is restored.

It is important to note that the embodiments of the present invention employ a routine which can be stored in the microprocessor and logic control circuit's internal RAM or ROM, or may be implemented using a discrete integrated circuit separate from the microprocessor and logic control circuit. Thus, the present invention does not require much, if any, additional hardware in the implantable cardiac stimulating device. In addition, the present invention may be implemented in existing dedicated cardioverter/defibrillators, as well as devices providing pacing capabilities.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 3 is an example of a truth table used by the microprocessor and logic control circuit shown in FIG. 1 in selecting and setting energy values for a therapeutic shock.

DETAILED DESCRIPTION OF THE PREFERRED EMBODIMENT

Figure 1:
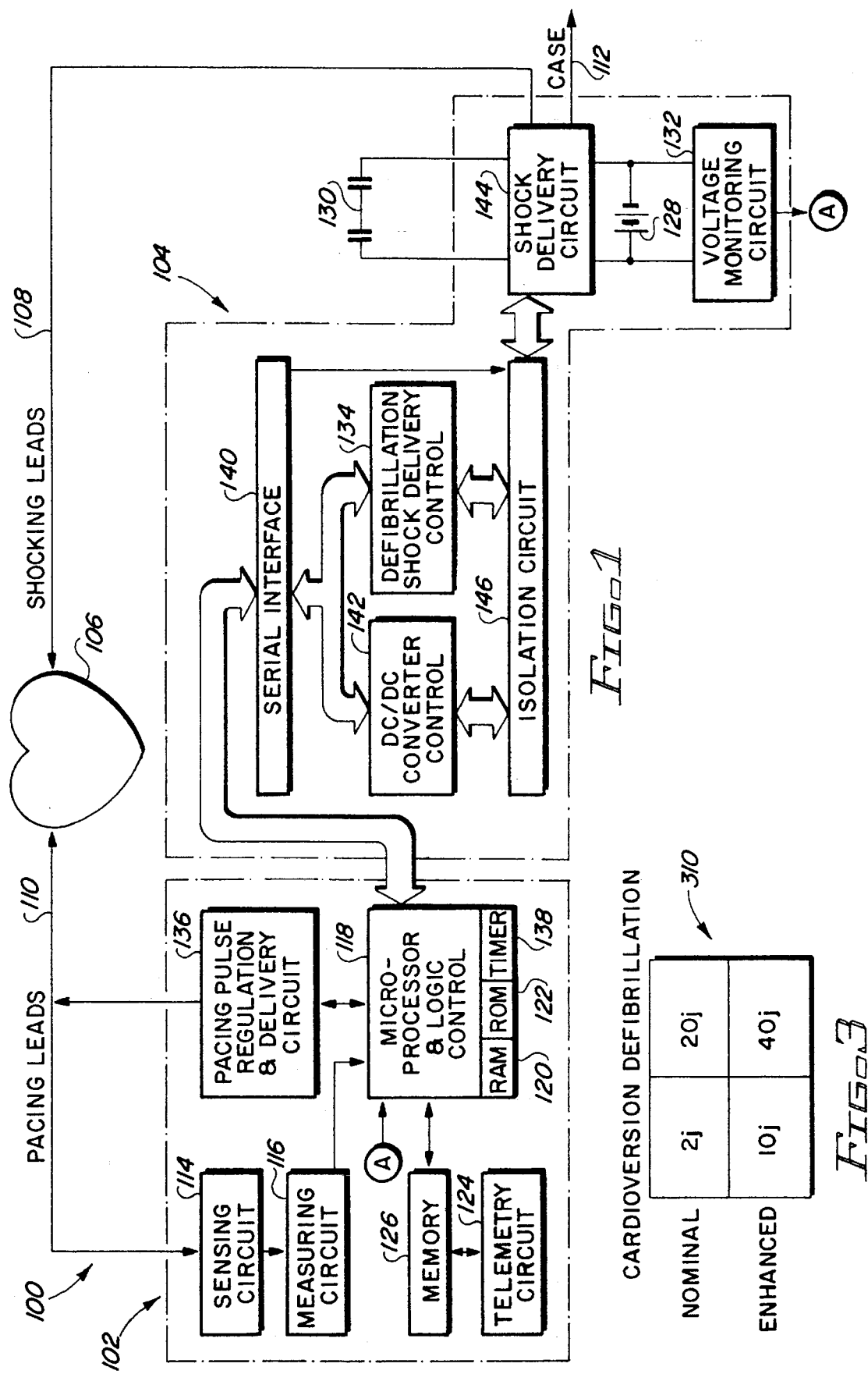
FIG. 1 is a block diagram of an implantable cardiac stimulating device which includes a system for increasing shock energy as function of elapsed times-to-therapy in accordance with the principles of the present invention.

Referring to FIG. 1, a block diagram representing an implantable cardiac stimulating device 100 which increases therapeutic shock energy as a function of an elapsed time-to-therapy in accordance with the principles of the present invention is described. The implantable cardiac stimulating device 100 includes circuitry 102 which is responsible for regulation and delivery of pacing therapy as well as overall operational control of the implantable cardiac stimulating device 100. Also included is circuitry 104 dedicated to the control, generation, and delivery of cardioversion and defibrillation shocks.

The implantable cardiac stimulating device 100 preferably administers therapeutic shocks (i.e., cardioversion or defibrillation shocks) or pacing pulses to a patient's heart 106 in order to interrupt cardiac arrhythmias or supply antitachycardia pacing, respectively. However, the present invention also may be practiced with dedicated implantable cardioverters and defibrillators.

The implantable cardiac stimulating device 100 delivers the therapeutic cardioversion or defibrillation shocks to the patient's heart 106 through a plurality of shocking leads 108. Low energy pacing pulses are administered to the patient's heart 106 through a pacing lead system 110. The pacing lead system 110 also serves to sense intrinsic cardiac activity during periods when electrical stimulation is not being applied to the heart 106. Further, an electrically conductive enclosure 112 of the implantable cardiac stimulating device 100 may be used as an electrode in the delivery of therapeutic shocks or pacing pulses.

The lead system 110 feeds physiological and electrophysiological data in the form of analog signals from the patient's heart 106 to a sensing circuit 114. The lead system 110 may also include sensors (not shown) which monitor cardiac mechanical activity, as described in commonly-assigned, copending U.S. patent application Ser. No. 08/091,636, filed Jul. 14, 1993 of Causey and Moberg, entitled "Implantable Leads Incorporating Wall Motion Sensors and Method of Fabrication and a System and Method for Detecting Cardiac Arrhythmias Using a Cardiac Wall Motion Sensor Signal."

The sensing circuit 114 typically amplifies the incoming analog signals and filters out unwanted noise. These amplified analog signals are then sent to a measuring circuit 116 where the signals are digitized and formatted for use by a microprocessor and logic control circuit 118. The microprocessor and logic control circuit 118 then analyzes the received digital signals to determine the existence of an arrhythmia.

The microprocessor and logic control circuit 118 performs this analysis using routines located in RAM 120 or ROM 122. The RAM 120 or ROM 122 is preferred over an external discrete memory device (not shown) because of the savings in processing speed, power consumption and their effect on the overall size of the implantable cardiac stimulating device 100.

Communication with and programming of the device 100 is accomplished by a programmer (not shown) which communicates with the device 100 through a telemetry circuit 124. Telemetry data are transmitted to the microprocessor and logic control circuit 118 through a memory 126.

Prior to the detection of an arrhythmia, the microprocessor and logic control circuit 118 monitors the actual voltage of a battery 128—used to charge a pair of capacitors 130 as more fully described below—from which it forecasts a minimum time-to-therapy. Other device operational parameters which may be monitored by the device include capacitor discharge times, and any delays that are programmed into the device, such as those needed to properly synchronize a cardioversion shock with the ECG wave patterns. The actual voltage of the battery 128 is determined by a voltage monitoring circuit 132, which communicates this information to the microprocessor and logic control circuit 118.

If the microprocessor and logic control circuit 118 determines that, should a therapeutic cardioversion or defibrillation shock be needed, a forecasted time-to-therapy equals or exceeds a critical time, it instructs a defibrillation shock delivery control circuit 134 to set the energy level of the shock to be delivered to a predetermined increased shock energy value. If the forecasted time-to-therapy does not equal or exceed the critical time, the microprocessor and logic control circuit 118 instructs the defibrillation shock delivery control circuit 134 to set the shock energy level to a nominal value. This occurs before the detection of an arrhythmia and is continually updated.

If pacing pulses are needed, for example, to treat bradycardia, the microprocessor and logic control circuit 118 enables a pacing pulse regulation and delivery circuit 136, which generates and transmits the pulses to the patient's heart 106 at the appropriate times through leads selected by the microprocessor and logic control circuit 118 from the pacing lead system 110.

In response to a detected tachycardia, the microprocessor and logic control circuit 118 starts the running of a timer 138 and, through a serial interface 140, instructs a DC/DC converter control circuit 142 to begin charging the pair of capacitors 130 in series with each other to their target voltage. The DC/DC converter control circuit 142, in turn, instructs a shock delivery circuit 144, through an isolation circuit 146, to begin charging the capacitors 130. The DC/DC converter control circuit 142 performs all the control and logic operations needed by the shock delivery circuit 144 to create a high frequency, rectified DC high voltage for application to the capacitors 130. The defibrillation shock delivery control circuit 134 performs all the logic and control operations needed to deliver a desired therapeutic shock to the heart 106. That includes controlling the delivery, energy content, and waveform of a therapeutic shock.

In a preferred embodiment, the isolation circuit 146 includes a transformer interface (not shown) which is used to electrically isolate the low voltage circuits of both the defibrillation shock delivery control circuit 134 and the DC/DC converter control circuit 142 as well as the circuitry 102 from exposure to high voltages. All control and feedback signals preferably pass through the isolation circuit 146 in order to prevent harm to the low voltage circuits of the device 100.

A high voltage charge is typically generated in the following manner: the battery 128 supplies a voltage typically on the order of 6.4 volts to the shock delivery circuit 144. When instructed to do so by the DC/DC converter control circuit 142, and preferably by employing a DC/DC converter (not shown), which may be of conventional design, the shock delivery circuit 144 produces a high frequency pulsed voltage substantially equal in magnitude to the voltage of the battery 128. The high frequency pulsed low voltage is converted to high frequency pulsed high voltage by a step-up transformer (not shown). This high frequency high voltage is then full-wave rectified by the shock delivery circuit 144. The rectified signal is applied to the capacitors 130. The capacitors 130 charge incrementally with each rectified pulse to a voltage corresponding to either the nominal or increased shock energy level depending upon which one is set to be delivered. The shock delivery circuit 144 informs the defibrillation shock delivery control circuit 134, through the isolation circuit 146, when the capacitors 130 are sufficiently charged (i.e., charged to their target voltage).

By analyzing the digitized signals provided by the measuring circuit 116, the microprocessor and logic control circuit 118 ultimately determines the type of arrythmia occurring. As a result of this continuing analysis, the arrhythmia is identified as, for example, either VT or VF. This determination prescribes a predetermined range of shock energies to be delivered corresponding to the different therapeutic energy ranges for the occurring cardiac event. For example, if the microprocessor and logic control circuit 118 determines that the patient is undergoing cardiac fibrillation and the defibrillation shock delivery control circuit 134 has been set to administer an enhanced energy therapeutic shock, a shock of about 40 joules may be appropriate. Because each patient must be evaluated on an individual basis, it is contemplated that the present invention will allow a physician to preselect a therapeutic energy value appropriate for a given type of arrhythmia for both nominal and enhanced energy shocks.

Once the defibrillation shock delivery control circuit 134 is informed that capacitors 130 are sufficiently charged, and the shock energy level has been set, the microprocessor and logic control circuit 118 preferably compares the elapsed time-to-therapy, as kept by timer 138, to the critical time. If the elapsed time-to-therapy is less than the critical time, the microprocessor and logic control circuit 118 instructs the defibrillation shock delivery control circuit 134 to administer the nominal shock energy value. However, if the elapsed time-to-therapy is equal to or greater than the critical time, the microprocessor and logic control circuit 118 instructs the defibrillation shock delivery control circuit 134 to set the shock energy level to the enhanced shock energy level and the capacitors 130 are further charged to a corresponding voltage level. The microprocessor and logic control circuit 118 then instructs the defibrillation shock delivery control circuit 134 to direct the shock delivery circuit 144 to administer the shock. Thus, the initial energy value of the therapeutic shock may be overridden by the elapsed time-to-therapy determination.

It should be noted that use of the term defibrillation shock delivery control circuit 134 is not intended to mean that only defibrillation shocks are controlled, but includes control of all shocks other than pacing pulses.

Figure 2:
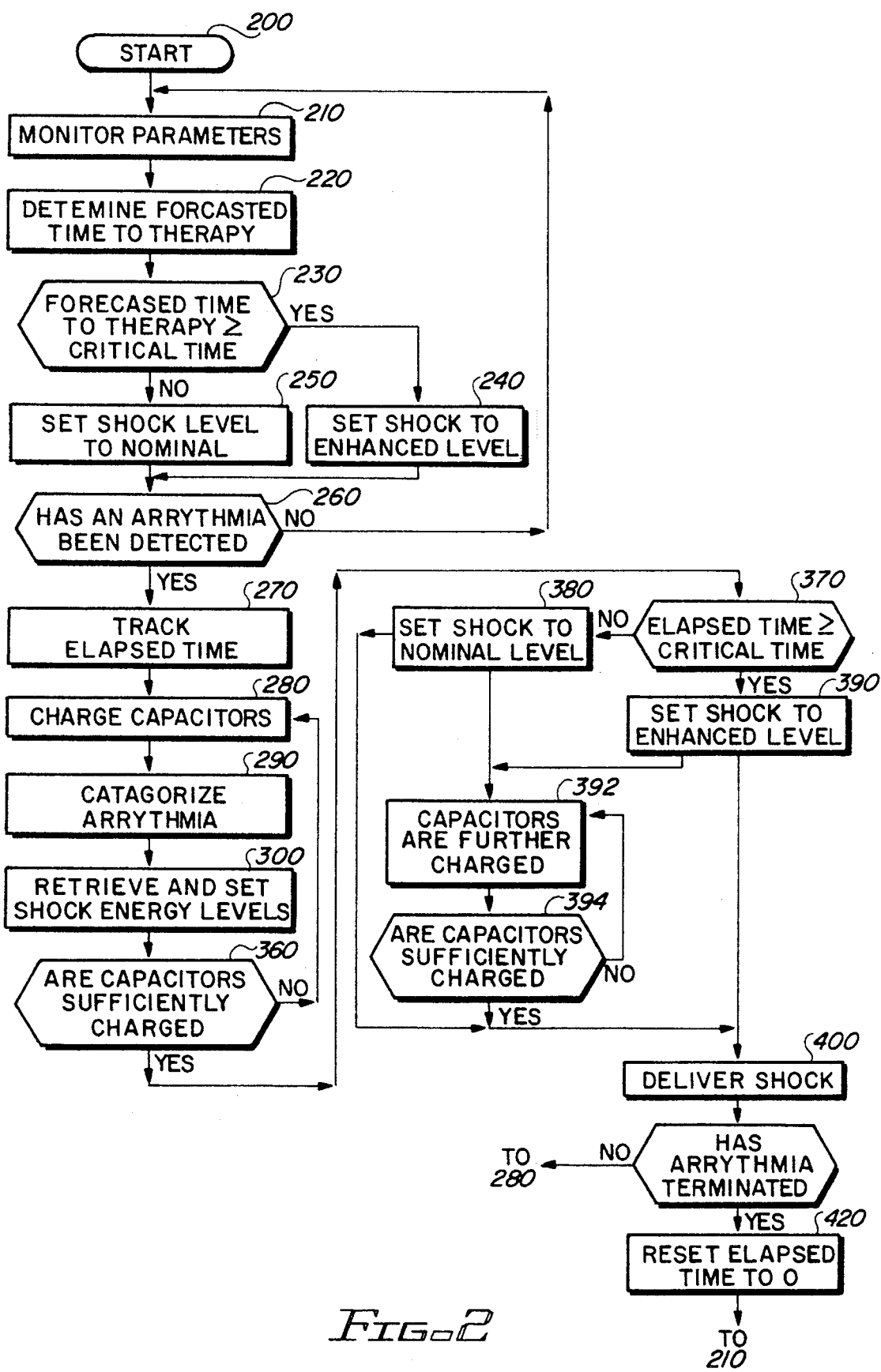
FIG. 2 is a logic flow diagram representing a program executed by the microprocessor and logic control circuit shown in FIG. 1.

Referring now to FIG. 2, a logic flow diagram is described representing a control program executed by the microprocessor and logic control circuit 118 of FIG. 1. The control program is initiated at a start 200 when a start-up command is received by the telemetry circuit 124 (FIG. 1). At a step 210, the microprocessor and logic control circuit 118 (FIG. 1) monitors certain device operational parameters. The monitored device operational parameters may include any of those items mentioned above which can prolong the time-to-therapy. In the interest of clarity, the following description is presented in terms of an example using two parameters, namely, battery voltage and past failed reversion attempts.

At a step 220, the microprocessor and logic control circuit 118 (FIG. 1) determines the forecasted time-to-therapy as a function of the voltage of the battery 128 (FIG. 1) as measured by the voltage monitoring circuit 132 (FIG. 1). That determination may be made by employing the known relationship between capacitor charge time and battery potential or, alternatively, by referring to a matrix or lookup table (not shown) cross-referencing capacitor charge times with battery potential.

At a test 230, the microprocessor and logic control circuit 118 (FIG. 1) determines whether the forecasted time-to-therapy equals or exceeds the critical time. If, at the test 230, the microprocessor and logic control circuit 118 (FIG. 1) determines that the forecasted time-to-therapy does equal or exceed the critical time, at a step 240 the microprocessor and logic control circuit 118 (FIG. 1) instructs the defibrillation shock delivery control circuit 134 (FIG. 1) to set the therapeutic shock to be delivered to an increased shock energy value. If at the test 230, the microprocessor and logic control circuit 118 (FIG. 1) determines that the forecasted time-to-therapy does not equal or exceed the critical time, the microprocessor and logic control circuit 118 (FIG. 1) instructs the defibrillation shock delivery control circuit 134 (FIG. 1) to set the therapeutic shock to be delivered to a nominal shock energy level at a step 250.

At a test 260, the microprocessor and logic control circuit 118 (FIG. 1) determines whether an arrythmia exists by analyzing signals received from the measuring circuit 116 (FIG. 1). The microprocessor and logic control circuit 118 (FIG. 1) cycles through steps 210 through 260 until an arrhythmia is detected. During that cycling, any further degradation of battery voltage is incorporated into the current determination of whether the forecasted time-to-therapy equals or exceeds the critical time.

Once an arrhythmia is detected at the test 260, the microprocessor and logic control circuit 118 (FIG. 1) causes the timer 138 (FIG. 1) to begin tracking the elapsed time-to-therapy at a step 270. At a step 280, the capacitors 130 (FIG. 1) are charged to their target potential. At a step 290, the microprocessor and logic control circuit 118 (FIG. 1) proceeds to categorize the arrhythmia. At a step 300, predetermined energy levels for the nominal and enhanced shock energy levels for both cardioversion and defibrillation are retrieved from the RAM 120 (FIG. 1) and are communicated to the defibrillation shock delivery control circuit 134 (FIG. 1). The capacitors 130 (FIG. 1) are charged to a voltage corresponding to the set shock level.

Referring now to FIG. 3, an example of the selection of shock energy levels is described. FIG. 3 shows a 2×2 matrix or lookup table 310 having a selected nominal energy level and a selected enhanced energy level for both cardioversion and defibrillation shocks. A physician may select a nominal energy level of 2 joules for cardioversion and a nominal energy level of 20 joules for defibrillation. As stated, a shock of the nominal energy level is administered when the critical time is not equaled or exceeded by the forecasted time-to-therapy or the elapsed time-to=therapy (which can override a determination based on the forecasted time-to-therapy). Conversely, a shock of the enhanced energy level is administered when the forecasted time-to-therapy or the elapsed time-to-therapy equals or exceeds the critical time. The nominal and enhanced energy levels for both cardioversion and defibrillation are preferably selected by the physician through the use of an external programmer (not shown). According to the principles of the present invention, the enhanced energy level should be substantially greater than the nominal energy level (e.g., 10 joules for cardioversion and 40 joules for defibrillation).

As stated, the period of time after which the energy requirement for highly successful cardioversion or defibrillation is significantly increased is termed the critical time. Not surprisingly, the critical time will vary from individual to individual. The physician, being most knowledgeable about the physical condition of the patient and the ailment being treated, is best suited to prescribe the critical time. Thus, the critical time is preferably preset by the physician either before or after implanting the device 100 (FIG. 1).

Referring again to FIG. 2, at a test 360, the shock delivery circuit 144 (FIG. 1) determines whether the capacitors 130 (FIG. 1) are sufficiently charged. When the capacitors 130 (FIG. 1) are sufficiently charged, at a test 370, the microprocessor and logic control circuit 118 (FIG. 1) is informed of their ready state as described above and proceeds to determine whether the elapsed time-to-therapy equals or exceeds the critical time. Preferably, projected capacitor discharge time is considered along with the elapsed time at this point to forecast the actual elapsed time-to-therapy. If at the test 370 the microprocessor and logic control circuit 118 (FIG. 1) determines that the elapsed time-to-therapy does not equal or exceed the critical time, at a step 380, a shock of the nominal energy level is set to be delivered. Conversely, if at the test 370 the microprocessor and logic control 118 (FIG. 1) determines that the elapsed time-to-therapy equals or exceeds the critical time, at a step 390 a shock of the enhanced energy value is set to be delivered and capacitors 130 (FIG. 1) are further charged to the appropriate voltage at a step 392. At a test 394, the microprocessor and logic control determines whether or not the capacitors are sufficiently charged. If the capacitors 130 (FIG. 1) are not sufficiently charged, the routine cycles to the step 392

The determination by the microprocessor and logic control 118 (FIG. 1) based on the forecasted time-to-therapy at the test 230 is overridden by a conflicting determination based on the elapsed time-to-therapy at the test 370. Because of the precise nature by which the determination of the test 230 is made, it is contemplated that it will typically not conflict with the determination made at the test 370, and thus will not be overridden often. If the capacitors 130 (FIG. 1) are sufficiently charged, then at a step 400, the defibrillation shock delivery control circuit 134 (FIG. 1) instructs the shock delivery circuit 144 (FIG. 1) to deliver the therapeutic shock of the set energy level and the shock delivery circuit 144 (FIG. 1) responds accordingly.

At a test 410, the microprocessor and logic control circuit 118 (FIG. 1) determines whether the arrhythmia has been terminated. If the arrhythmia has not been terminated, the device cycles back to step 280 where the capacitors 130 (FIG. 1) are recharged and steps 290 through 410 are repeated. The timer 138 (FIG. 1) continues to track time after the onset of the arrhythmia and by doing so incorporates delays due to past failed reversion attempts into subsequent determinations of whether the critical time is exceeded. This cycle continues until it is determined at the test 410 that the arrhythmia has been terminated.

At a step 420, after the arrhythmia has been terminated, the timer 138 (FIG. 1) is reset to a initial value of zero and the device is put back into the monitoring cycle of the steps 210 through 260.

Thus, a system and method for automatically adjusting the energy content of a therapeutic shock as a function of time-to-therapy is provided. One skilled in the art will appreciate that the present invention can be practiced by other than the described embodiments, which are presented for purposes of illustration and not of limitation, and the present invention is limited only by the claims that follow.

What is claimed is:

1. An implantable cardiac stimulating device for administering therapeutic shocks to a patient's heart to interrupt cardiac arrhythmias, the device comprising:

shock generation and delivery circuitry for generating a therapeutic shock at one of (a) a nominal energy level, and (b) an increased energy level, and delivering the therapeutic shock to the patient's heart, the shock generation and delivery circuitry requiring an amount of time from the onset of a cardiac arrhythmia to generate and deliver the therapeutic shock, the amount of time varying as a function of a device operational parameter; and control means for detecting the onset of a cardiac arrhythmia, for monitoring the device operational parameter to forecast the amount of time required from the onset of a cardiac arrhythmia for the shock generation and delivery circuitry to generate and deliver the therapeutic shock, for causing the shock generation and delivery circuitry to generate and deliver the therapeutic shock at the nominal energy level when the forecasted time is less than a prescribed critical time, and for causing the shock generation and delivery circuitry to generate and deliver the therapeutic shock at the increased energy level when the forecasted time equals or exceeds the prescribed critical time.

2. The implantable cardiac stimulating device of claim 1, wherein the shock generation and delivery circuitry comprises:

a battery for supplying energy used to generate the therapeutic shock, the battery having a measurable battery voltage, the battery voltage being a device operational parameter; and a battery monitoring circuit for monitoring the battery voltage and for communicating the battery voltage to the control circuitry.

3. The implantable cardiac stimulating device of claim 2, wherein the control means comprises means for interrogating the battery at pre-determined time intervals.

4. The implantable cardiac stimulating device of claim 1, wherein the control circuitry comprises a memory circuit for storing values representing the nominal and enhanced energy levels for the therapeutic shock.

5. The implantable cardiac stimulating device of claim 4, wherein the control circuitry further comprises a telemetry circuit for receiving the values representing the nominal and enhanced energy levels from an external programming unit.

6. The implantable cardiac stimulating device of claim 1, wherein the control circuitry comprises a timer for measuring elapsed time from the onset of a cardiac arrhythmia to a moment immediately preceding delivery of the therapeutic shock by the shock generation and delivery circuitry, wherein the control circuitry causes the shock generation and delivery circuitry to generate and deliver the therapeutic shock at the nominal energy level when the elapsed time is less than the prescribed critical time, and causes the shock generation and delivery circuitry to generate and deliver the therapeutic shock at the increased energy level when the elapsed time equals or exceeds the prescribed critical time, whereby the energy level selection based on the elapsed time supersedes the energy level selection based on the forecasted time.

7. A method of administering therapeutic shocks from an implantable cardiac stimulating device to a patient's heart to interrupt cardiac arrhythmias, the method comprising the steps of:

detecting the onset of a cardiac arrhythmia;

monitoring the device operational parameter to forecast the amount of time required from the onset of a cardiac arrhythmia to generate and deliver the therapeutic shock;

selecting the nominal energy level for the therapeutic shock when the forecasted time is less than a prescribed critical time;

selecting the increased energy level for the therapeutic shock when the forecasted time equals or exceeds the prescribed critical time; and generating a therapeutic shock at one of (a) a nominal energy level, and (b) an increased energy level, and delivering the therapeutic shock to the patient's heart, wherein an amount of time from the onset o a cardiac arrhythmia is required to generate and deliver the therapeutic shock, the amount of time varying as a function of a device operational parameter.

8. The method of claim 7, wherein the monitoring step comprises monitoring the voltage of a battery used to supply energy for generating the therapeutic shock, the battery voltage being a device operational parameter.

9. The method of claim 8, wherein the battery voltage is monitored at predetermined time intervals.

10. The method of claim 7, further comprising the step of storing values representing the nominal and increased energy levels for the therapeutic shock in a memory.

11. The method of claim 10, further comprising the step of telemetrically receiving the values representing the nominal and enhanced energy levels from an external programming unit.

12. The method of claim 7 further comprising the steps of:

measuring elapsed time from the onset of a cardiac arrhythmia to a moment immediately preceding delivery of the therapeutic shock;

selecting the nominal energy level for the therapeutic shock when the elapsed time is less than the prescribed critical time; and selecting the increased energy level for the therapeutic shock when the elapsed time equals or exceeds the prescribed critical time;

wherein the energy level selection based on the elapsed time supersedes the energy level selection based on the forecasted time.

13. An implantable cardiac stimulating device for administering therapeutic shocks to a patient's heart to interrupt cardiac arrhythmias, the device comprising:

means for generating a therapeutic shock at one of (a) a nominal energy level, and (b) an enhanced energy level, and delivering the therapeutic shock to the patient's heart in response to a cardiac arrhythmia;

a battery for supplying energy used to generate the therapeutic shock, the battery having a measurable battery voltage;

means for measuring the battery voltage; and means for selecting the nominal energy level for the therapeutic shock when the battery voltage equals or exceeds a prescribed threshold voltage and for selecting the enhanced energy level for the therapeutic shock when the battery voltage is below the prescribed threshold voltage.

14. An implantable cardiac stimulating device for administering therapeutic shocks to a patient's heart to interrupt cardiac arrhythmias, the device comprising:

means for forecasting a time-to-therapy as a function of the device operational parameters;

means for generating a therapeutic shock having an energy level defined as a function of the forecasted time-to-therapy, the generating means including a battery;

means for detecting the onset of a cardiac arrhythmia; and means for delivering the therapeutic shock to the patient's heart.

15. The implantable cardiac stimulating device of claim 14, wherein the operational parameters includes battery voltage.

* * * * *